(12) United States Patent
Page et al.

(10) Patent No.: US 10,718,000 B2
(45) Date of Patent: *Jul. 21, 2020

(54) GENES AND PROTEINS FOR AROMATIC POLYKETIDE SYNTHESIS

(71) Applicants: National Research Council of Canada, Ottawa (CA); University of Saskatchewan, Saskatoon (CA)

(72) Inventors: Jonathan E. Page, Saskatoon (CA); Steve Gagne, Aberdeen (CA)

(73) Assignees: National Research Council of Canada, Ottawa (CA); University of Saskatchewan, Saskatoon (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/051,701

(22) Filed: Aug. 1, 2018

(65) Prior Publication Data

US 2019/0169661 A1 Jun. 6, 2019

Related U.S. Application Data

(63) Continuation of application No. 15/438,291, filed on Feb. 21, 2017, now Pat. No. 10,059,971, which is a continuation of application No. 13/641,272, filed as application No. PCT/CA2011/000428 on Apr. 15, 2011, now Pat. No. 9,611,460.

(60) Provisional application No. 61/324,343, filed on Apr. 15, 2010.

(51) Int. Cl.
| | |
|---|---|
| *C12N 15/70* | (2006.01) |
| *C12N 15/81* | (2006.01) |
| *C12P 17/06* | (2006.01) |
| *C12N 15/52* | (2006.01) |
| *C12P 7/22* | (2006.01) |

(52) U.S. Cl.
CPC .............. *C12P 17/06* (2013.01); *C12N 15/52* (2013.01); *C12N 15/70* (2013.01); *C12P 7/22* (2013.01); *C12Y 404/01026* (2015.07)

(58) Field of Classification Search
None
See application file for complete search history.

(56) References Cited

U.S. PATENT DOCUMENTS

| | | | |
|---|---|---|---|
| 9,611,460 B2 | 4/2017 | Page et al. | |
| 10,059,971 B2 * | 8/2018 | Page ............. | C12Y 203/01206 |
| 2002/0023280 A1 | 2/2002 | Gorlach et al. | |
| 2003/0180945 A1 | 9/2003 | Wang et al. | |
| 2012/0144523 A1 | 6/2012 | Page et al. | |

FOREIGN PATENT DOCUMENTS

| | | |
|---|---|---|
| JP | 2000-078979 | 3/2000 |
| JP | 2001-029082 | 2/2001 |
| WO | 2011017798 A1 | 2/2011 |
| WO | 2015196275 A1 | 12/2015 |

OTHER PUBLICATIONS

Marks et al, 2009, J. Exp. Bot. 60; 3715-3726.*
Alvarez, John Paul et al., Endogenous and synthetic microRNAs stimulate simultaneous, efficient, and localized regulation of multiple targets in diverse species. Plant Cell (2006) 18:1134-51.
Bechtold N, Ellis J, Pelletier G (1993) in planta Agrobacterium-mediated gene transfer by infiltration of adult Arabidopsis thaliana plants. C R Acad Sci Paris, Sciences de la vie/Life sciences 316: 1194-1199.
Becker D. et al., Fertile transgenic wheat from microprojectile bombarment of scutellar tissue, The Plant Journal (1994) 5, (2), 299-307.
Collakova Eva, et al., Isolation and Functional Analysis of Homogentisate Phytyltransferase from Synechocystis sp. PCC 6803 and Arabidopsis, Plant Physiology, Nov. 2001, vol. 127, pp. 1113-1124.
Datla, R, Anderson JW, Selvaraj G, Trends in Biotechnology. 13: 332-337; (1997) Plant promoters for transgene expression. Biotechnology Annual Review 3: 269-296.
Deblock M, DeBrouwer D, Tenning P (1989) Transformation of Brassica napus and Brassica oleracea using Agrobacterium tumefaciens and the expression of the bar and neo genes in the transgenic plants. Plant Physiol. 91: 694-701.
Depicker A, Montagu MV (1997) Post-transcriptional gene silencing in plants. Curr Opin Cell Biol. 9: 373-82.
Fellermeier Monika, et al., Prenylation of olivetolate by a hemp transferase yields cannabigerolic acid, the precursor of tetrahydrocannabinol, FEBS Letters 427 (1998) 283-285.
Gen Bank Accession No. NP_001060083 dated Jun. 8, 2010.
Helliwell CA, Waterhouse PM (2005) Constructs and methods for hairpin RNA-mediated gene silencing in plants. Methods Enzymology 392:24-35.
Henikoff S, Till BJ, Comai L (2004) Tilling. Traditional mutagenesis meets functional genomics. Plant Physiol 135:630-6.
International Preliminary Examination Report dated Oct. 16, 2012 based on PCT/CA2011/00428.
International Search Report dated Jul. 29, 2011 based on PCT/CA2011/000428.
Katavic V, Haughn GW, Reed D, Martin M, Kunst L (1994) In planta transformation of *Arabidopsis thaliana*. Mol. Gen. Genet. 245: 363-370.
Katsuyama Yohei, Synthesis of Unnatural Flavonoids and Stilbenes by Exploiting the Plant Biosynthetic Pathway in *Escherichia coli*, Chemistry & Biology 14, 613-621, Jun. 2007.

(Continued)

*Primary Examiner* — Jason Deveau Rosen
(74) *Attorney, Agent, or Firm* — Carmela De Luca; Bereskin & Parr LLP

(57) ABSTRACT

Nucleic acid molecules encoding polypeptides having polyketide synthase activity have been identified and characterized. Expression or over-expression of the nucleic acids alters levels of cannabinoid compounds in organisms. The polypeptides may be used in vivo or in vitro to produce cannabinoid compounds.

11 Claims, 6 Drawing Sheets

Specification includes a Sequence Listing.

(56) References Cited

OTHER PUBLICATIONS

Leonard Effendi et al., Strain Improvement of Recombinant *Escherichia coli* for Efficient Production of Plant Flavonoids vol. 5, No. 2, 257-265 Molecular Pharmaceutics.
Li X, Lassner M, Zhang Y. (2002) Deleteagene: a fast neutron deletion mutagenesis-based gene knockout system for plants. Comp Funct Genomics. 3: 158-60.
Lithwick G, Margalit H (2003) Hierarchy of sequence-dependent features associated with prokaryotic translation. Genome Research 13: 2665-73.
Marks MD, Tian L, Wenger JP, Omburo SN, Soto-Fuentes W, He J, Gang DR, Weiblen GD, Dixon RA. (2009) Identification of candidate genes affecting Delta9-tetrahydrocannabinol biosynthesis in Cannabis sativa. J Exp Bot. 60, 3715-3726.
Meyer P (1995) Understanding and controlling transgene expression. Trends in Biotechnology. 13: 332-337.
Moloney MM, Walker JM, Sharma KK (1989) High efficiency transformation of Brassica napus using Agrobacterium vectors. Plant Cell Rep. 8: 238-242.
Morimoto S, Komatsu K, Taura F, Shoyama,Y. (1998) Purification and characterization of cannabichromenic acid synthase from Cannabis sativa. Phytochemistry. 49: 1525-1529.
Needleman and Wunsch. A General Method Applicable to the Search for Similarities in the Amino Acid Sequence of Two Proteins. J. Mol. Biol. 48: 443 (1970).
Nehra, Narender S., et al., Self-fertile transgenic wheat plants regenerated from isolated scutellar tissues following microprojectile bombardment with two distinct gene constructs, The Plant Journal (1994) 5 (2), 285-297.
Page J., Nagel J. (2006) Biosynthesis of terpenophenolics in hop and cannabis. In JT Romeo, ed, Integrative Plant Biochemistry, vol. 40. Elsevier, Oxford, pp. 179-210.
Pearson and Lipman. Improved tools for biological sequence comparison. Proc. Natl. Acad. Sci. (U.S.A.) 85: 2444 (1988).
Potrykus I (1991) Gene transfer to plants: Assessment of published approaches and results. Annu. Rev. Plant Physiol. Plant Mol. Biol. 42: 205-225.
Ralston Lyle, et al., Partial Reconstruction of Flavonoid and Isoflavonoid Biosynthesis in Yeast Using Soybean Type I and Type II Chalcone Isomerases, Plant Physiology, Apr. 2005, vol. 137, pp. 1375-1388.
Rhodes CA, Pierce DA, Mettler IJ, Mascarenhas D, Detmer JJ (1988) Genetically transformed maize plants from protoplasts. Science 240: 204-207.
Sanford JC, Klein TM, Wolf ED, Allen N (1987) Delivery of substances into cells and tissues using a particle bombardment process. J. Part. Sci. Technol. 5: 27-37.
Schwab R, Ossowski S, Riester M, Warthmann N, Weigel D (2006) Highly specific gene silencing by artificial microRNAs in Arabidopsis. Plant Cell 18:1121-33.
Shimamoto, Ko, et al., Fertile transgenic rice plants regenerated from transformed protoplasts, Nature, vol. 338, 1989.
Shoyama Y, Hirano H, Nishioka I. (1984) Biosynthesis of propyl cannabinoid acid and its biosynthetic relationship with pentyl and methyl cannabinoid acids. Phytochemistry. 23(9): 1909-1912.
Sirikantaramas S, Taura F, Tanaka Y, Ishikawa Y, Morimoto S, Shoyama Y. (2005) Tetrahydrocannabinolic acid synthase, the enzyme controlling marijuana psychoactivity, is secreted into the storage cavity of the glandular trichomes. Plant Cell Physiol. 46: 1578-1582.
Sirikantaramas S, et al., The Gene Controlling Marijuana Psychoactivity Molecular Cloning and Heterologous Expression of 1-Tetrahydrocannabinolic Acid Synthase From Cannabis Sativa L, The Journal of Biological Chemistry, vol. 279, No. 38, Issue of Sep. 17, pp. 39767-39774, 2004.
Smith and Waterman, Ad. Comparison of Biosequences. Advances in Applied Mathematics,2: 482 (1981).
Songstad DD, Somers DA, Griesbach RJ (1995) Advances in alternative DNA delivery techniques. Plant Cell Tissue Organ Cult. 40:1-15.
Stam M, de Bruin R, van Blokland R, van der Hoorn RA, Mol JN, Kooter JM (2000).
Taura F, Morimoto S, Shoyama Y, Mechoulam R. (1995) First direct evidence for the mechanism of 1-tetrahydrocannabinolic acid biosynthesis. J Am Chem Soc. 117: 9766-9767.
Taura F, Morimoto S, Shoyama Y. (1996) Purification and characterization of cannabidiolic-acid synthase from Cannabis sativa L. Biochemical analysis of a novel enzyme that catalyzes the oxidocyclization of cannabigerolic acid to cannabidiolic acid. J Biol Chem. 271: 17411-17416.
Taura F, Sirikantaramas S, Shoyama Y, Yoshikai K, Shoyama Y, Morimoto S. (2007) Cannabidiolic-acid synthase, the chemotype-determining enzyme in the fiber-type Cannabis sativa. FEBS Lett. 581: 2929-2934.
Taura F, Tanaka S, Taguchi C, Fukamizu T, Tanaka H, Shoyama Y, Morimoto, S. (2009) Characterization of olivetol synthase, Type III a polyketide synthase putatively involved in cannabinoid biosynthetic pathway. FEBS Lett. 583: 2061-2066.
Vasil I K (1994) Molecular improvement of cereals. Plant Mol. Biol. 25: 925-937.
Walden R, Wingender R (1995) Gene-transfer and plant regeneration technique. Trends in Biotechnology 13: 324-331.
Welch et al. (2009) Design parameters to control synthetic gene expression in *Escherichia coli*. PLoS One 4: e7002.
Written Opinion dated Jul. 29, 2011 based on PCT/CA2011/000428.
Zhang Haoran, Bacterial Hosts for Natural Product Production, Molecular Pharmaceutics vol. 5, No. 2, 212-225.
Gagne et al. Identification of olivetolic acid cyclase from Cannabis sativa reveals a unique catalytic route to plant polyketides 2012, PNAS, 109:12811-12816.
Taura. Production of Tetrahydrocannabinol by Transgenic Cultured Cells. 2004, NISR Research Grant, pp. 94-95.
Marks et al. Identification of candidate genes affecting Alpha9-tetrahydrocannabinol biosynthesis in Cannabis sativa. 2009, J. Exp. Botany, 60: 3715-3726.
Puigbo et al. Optimizer: a web server for optimizing the codon usage of DNA sequences. 2007, Nuc. Acid. Res., 35:W126-W131.
Marks et al, 2009, J. Exp. Botany, 60: 3715-3726, Supplemental Table 1.
Marks et al, 2009, J. Exp. Botany, 60: 3715-3726, Supplemental Table 2.
Lytle et al. Letter to the Editor: Structure of the hypothetical protein At3g17210 from *Arabidopsis thaliana*. 2004, J. Biomolecular NMR, 28: 397-400.
2015, Accession query_1311.
Schwab, Rebecca et al., Highly specific gene silencing by artificial microRNAs in Arabidopsis. Plant Cell (2006) 18:1121-33.

* cited by examiner

```
                        SEQUENCE LISTING

<160> NUMBER OF SEQ ID NOS: 5

<210> SEQ ID NO 1
<211> LENGTH: 303
<212> TYPE: DNA
<213> ORGANISM: Cannabis sativa

<400> SEQUENCE: 1
atggcagtga agcatttgat tgtattgaag ttcaaagatg aaatcacaga agcccaaaag     60
gaagaatttt caagacgta tgtgaatctt gtgaatatca tcccagccat gaaagatgta    120
tactggggta agatgtgac tcaaaagaat aaggaagaag gtacactca catagttgag    180 gtaacatttg agagtgtgga gactattcag gactacatta ttcatcctgc ccatgttgga    240
tttggagatg tctatcgttc tttctgggaa aaacttctca tttttgacta cacaccacga    300
aag                                                                 303

<210> SEQ ID NO 2
<211> LENGTH: 101
<212> TYPE: PRT
<213> ORGANISM: Cannabis sativa

<400> SEQUENCE: 2

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Val Asn
                20                  25                  30

Ile Ile Pro Ala Met Lys Asp Val Tyr Trp Gly Lys Asp Val Thr Gln
            35                  40                  45

Lys Asn Lys Glu Glu Gly Tyr Thr His Ile Val Glu Val Thr Phe Glu
        50                  55                  60

Ser Val Glu Thr Ile Gln Asp Tyr Ile Ile His Pro Ala His Val Gly
65                  70                  75                  80

Phe Gly Asp Val Tyr Arg Ser Phe Trp Glu Lys Leu Leu Ile Phe Asp
                85                  90                  95

Tyr Thr Pro Arg Lys
            100

<210> SEQ ID NO 3
<211> LENGTH: 303
<212> TYPE: DNA
<213> ORGANISM: Cannabis sativa

<400> SEQUENCE: 3
atggcggtta agcacttgat cgtcctgaag ttcaaagacg agattactga ggcccaaaaa     60
gaagagtttt caaaaccta cgtgaatctg gtgaacatca ttccggcgat gaaggacgtt    120
tactggggta agatgtgac ccagaagaac aaagaagagg ctatacccaa tattgtcgaa    180
gttacgtttg agagcgtcga accatccag gactatatca ttcatccggc acacgttggc    240
ttcggtgatg tgtatcgcag cttctgggag aaactgctga tctttgatta cacgccgcgt    300
aag                                                                 303
```

```
<210> SEQ ID NO 4
<211> LENGTH: 21
<212> TYPE: DNA
<213> ORGANISM: Cannabis sativa

<400> SEQUENCE: 4
atggcggtta agcacttgat c                                            21

<210> SEQ ID NO 5
<211> LENGTH: 21
<212> TYPE: DNA
<213> ORGANISM: Cannabis sativa

<400> SEQUENCE: 5
ttacttacgc ggcgtgtaat c                                            21
```

GENES AND PROTEINS FOR AROMATIC POLYKETIDE SYNTHESIS

CROSS-REFERENCE TO RELATED APPLICATIONS

This application is a continuation of U.S. patent application Ser. No. 15/438,291, filed Feb. 21, 2017, which is a continuation of U.S. patent application Ser. No. 13/641,272, filed Oct. 15, 2012, which is a National Stage Entry of International Application No. PCT/CA2011/000428, filed Apr. 15, 2011, which claims the benefit of U.S. Provisional Patent Application Ser. No. 61/324,343, filed Apr. 15, 2010, all of which are incorporated herein by reference in their entirety.

INCORPORATION OF SEQUENCE LISTING

A computer readable form of the Sequence Listing "P46230US02_SequenceListing.txt" (2,719 bytes), created on Jul. 31, 2018, is herein incorporated by reference.

FIELD OF THE INVENTION

The present invention relates to nucleic acid molecules and proteins involved in the synthesis of aromatic polyketides, and to uses of the nucleic acid molecules and proteins for producing cannabinoid compounds, and analogs thereof, and for altering cannabinoid production in organisms.

BACKGROUND OF THE INVENTION

*Cannabis sativa* L. (*Cannabis*, hemp, marijuana) is one of the oldest and most versatile domesticated plants, which today finds use as source of medicinal, food, cosmetic and industrial products. It is also well known for its use as an illicit drug owing to its content of psychoactive cannabinoids (e.g. $\Delta^9$-tetrahydrocannabinol, $\Delta^9$-THC). Cannabinoids and other drugs that act through mammalian cannabinoid receptors are being explored for the treatment of diverse conditions such as chronic pain, multiple sclerosis and epilepsy.

Cannabinoids have their biosynthetic origins in both polyketide and terpenoid metabolism and are termed terpenophenolics or prenylated polyketides (Page J., Nagel J. (2006) Biosynthesis of terpenophenolics in hop and *Cannabis*. In J T Romeo, ed, *Integrative Plant Biochemistry*, Vol. 40. Elsevier, Oxford, pp 179-210.). Cannabinoid biosynthesis occurs primarily in glandular trichomes that cover female flowers at a high density. Cannabinoids are formed by a three-step biosynthetic process: polyketide formation, aromatic prenylation and cyclization (see FIG. 1).

The first enzymatic step in cannabinoid biosynthesis is the formation of olivetolic acid by a putative polyketide synthase enzyme that catalyzes the condensation of hexanoyl coenzyme A (CoA) and malonyl CoA. A Type III polyketide synthase, termed "olivetol synthase" and referred to herein as polyketide synthase/olivetol synthase (CsPKS/olivetol synthase), from *Cannabis sativa* has recently been shown to form olivetol and several pyrone products but not olivetolic acid (Taura F, Tanaka S, Taguchi C, Fukamizu T, Tanaka H, Shoyama Y, Morimoto, S. (2009) Characterization of olivetol synthase, Type III a polyketide synthase putatively involved in cannabinoid biosynthetic pathway. *FEBS Lett.* 583: 2061-2066.). The nucleotide sequence of the gene encoding CsPKS/olivetol synthase is found in GenBank under accession number AB164375 with the polypeptide as accession BAG14339. The aforementioned products include the pyrones hexanoyltriacetic lactone (HTAL) and pentyldiacetic lactone (PDAL). The reason for the inability of this enzyme to form olivetolic acid, which is clearly a pathway intermediate based on the carboxylate structure of the cannabinoids, is not known. The lack of olivetolic acid formation by this polyketide synthase from *Cannabis* was confirmed by the inventors, as further described herein and also by Marks et al. (Marks M D, Tian L, Wenger J P, Omburo S N, Soto-Fuentes W, He J, Gang D R, Weiblen G D, Dixon R A. (2009) Identification of candidate genes affecting Delta9-tetrahydrocannabinol biosynthesis in *Cannabis sativa*. *J Exp Bot.* 60, 3715-3726.).

The second enzymatic step is the prenylation of olivetolic acid to form cannabigerolic acid (CBGA) by the enzyme geranylpyrophosphate:olivetolate geranyltransferase. This enzyme is an aromatic prenyltransferase and is the subject of commonly owned U.S. Provisional patent applications Ser. No. 61/272,057 filed Aug. 12, 2009 and U.S. Ser. No. 61/272,117 filed Aug. 18, 2009. CBGA is a central branch-point intermediate for the biosynthesis of the different classes of cannabinoids. Cyclization of CBGA yields $\Delta^9$-tetrahydrocannabinolic acid (THCA) or its isomers cannabidiolic acid (CBDA) or cannabichromenic acid (CBCA) (see FIG. 1). The Shoyama group has previously published the identification and purification of the three enzymes responsible for these cyclizations (Morimoto S, Komatsu K, Taura F, Shoyama, Y. (1998) Purification and characterization of cannabichromenic acid synthase from *Cannabis sativa*. *Phytochemistry.* 49: 1525-1529; Taura F, Morimoto S, Shoyama Y. (1996) Purification and characterization of cannabidiolic-acid synthase from *Cannabis sativa* L. Biochemical analysis of a novel enzyme that catalyzes the oxidocyclization of cannabigerolic acid to cannabidiolic acid. *J Biol Chem.* 271: 17411-17416; and Taura F, Morimoto S, Shoyama Y, Mechoulam R. (1995) First direct evidence for the mechanism of 1-tetrahydrocannabinolic acid biosynthesis. *J Am Chem Soc.* 117: 9766-9767). Cloning of THCA and CBDA synthases has also been previously published (Sirikantaramas S, Taura F, Tanaka Y, Ishikawa Y, Morimoto S, Shoyama Y. (2005) Tetrahydrocannabinolic acid synthase, the enzyme controlling marijuana psychoactivity, is secreted into the storage cavity of the glandular trichomes. *Plant Cell Physiol.* 46: 1578-1582.; Taura F, Sirikantaramas S, Shoyama Y, Yoshikai K, Shoyama Y, Morimoto S. (2007) Cannabidiolic-acid synthase, the chemotype-determining enzyme in the fiber-type *Cannabis sativa*. *FEBS Lett.* 581: 2929-2934. The genes for THCA synthase and CBDA synthase have been reported in Japan (Japanese Patent Publication 2000-078979; Japanese Patent Publication 2001-029082).

Cannabinoids are valuable plant-derived natural products. Genes encoding enzymes involved in cannabinoid biosynthesis will be useful in metabolic engineering of *Cannabis* varieties that contain ultra low levels of THC and other cannabinoids via targeted mutagenesis (e.g. TILLING) or other gene knockout techniques. Such genes may also prove useful for creation of specific *Cannabis* varieties for the production of cannabinoid-based pharmaceuticals, or for reconstituting cannabinoid biosynthesis in heterologous organisms such as bacteria or yeast, or for producing cannabinoids in cell-free systems that utilize recombinant proteins.

Genes encoding enzymes of cannabinoid biosynthesis can also be useful in synthesis of cannabinoid analogs and synthesis of analogs of cannabinoid precursors. Cannabinoid analogs have been previously synthesized and may be useful as pharmaceutical products.

There remains a need in the art to identify enzymes, and nucleotide sequences encoding such enzymes, that are involved in the synthesis of aromatic polyketides.

SUMMARY OF THE INVENTION

A novel gene from *Cannabis* has now been found which encodes a new polyketide forming enzyme that, acting together with the aforementioned *Cannabis sativa* polyketide synthase/olivetol synthase enzyme (CsPKS/olivetol synthase), catalyzes the formation of olivetolic acid. This newly discovered enzyme is termed *Cannabis sativa* olivetolic acid synthase (CsOAS). The CsPKS/olivetol synthase has polyketide synthase activity, while CsOAS functions as a polyketide cyclase to form olivetolic acid.

Thus, in a first aspect of the invention, there is provided an isolated or purified nucleic acid molecule comprising a nucleotide sequence having at least 75% sequence identity to SEQ ID NO: 1, or a codon degenerate sequence thereof.

In a second aspect of the invention, there is provided an isolated or purified nucleic acid molecule comprising a nucleotide sequence having at least 75% sequence identity to SEQ ID NO: 3, or a codon degenerate sequence thereof.

In a third aspect of the invention, there is provided an isolated or purified polypeptide comprising an amino acid sequence having at least 85% sequence identity to SEQ ID NO: 2, or a conservatively substituted amino acid sequence thereof.

In a fourth aspect of the invention, there is provided a vector, construct or expression system comprising a nucleic acid molecule of the invention.

In a fifth aspect of the invention, there is provided a host cell transformed with a nucleic acid molecule of the invention.

In a sixth aspect of the invention, there is provided a process of synthesizing a polyketide comprising: reacting an alkanoyl CoA with malonyl CoA in presence of a type III polyketide synthase enzyme and the polypeptide of the invention.

In an seventh aspect of the invention, there is provided a process of altering levels of cannabinoid compounds in an organism, cell or tissue comprising using a nucleic acid molecule of the present invention, or a part thereof, to silence in the organism, cell or tissue a gene that encodes an enzyme that catalyzes synthesis of an aromatic polyketide.

In an eighth aspect of the invention, there is provided a process of altering levels of cannabinoid compounds in an organism, cell or tissue comprising mutating genes in the organism, cell or tissue, and using the nucleic acid molecule of the present invention to select for organisms, cells or tissues containing mutants or variants of a gene that encodes an enzyme that catalyzes synthesis of an aromatic polyketide.

In a ninth aspect of the invention, there is provided a process of altering levels of cannabinoid compounds in an organism, cell or tissue comprising expressing or over-expressing a nucleic acid molecule of the invention in the organism, cell or tissue in comparison to a similar variety of organism, cell or tissue grown under similar conditions but without the expressing or over-expressing of the nucleic acid molecule.

In a tenth aspect of the invention, there is provided a process of synthesizing a naturally-occurring cannabinoid compound or a non-naturally occurring analog of a cannabinoid compound in an organism, cell or tissue comprising expressing the nucleic molecule of the invention in the organism, cell or tissue in the presence of a type III polyketide synthase enzyme, an alkanoyl CoA and malonyl CoA In an eleventh aspect of the present invention, there is provided a process of synthesizing a polyketide in an in vitro cell-free reaction, said process comprising: reacting acyl carboxylic acids with coenzyme A through the action of an acyl CoA synthetase to form alkanoyl CoAs in presence of a type III polyketide synthase enzyme and the polypeptide of the invention.

Polypeptides that are enzymes catalyzing the synthesis of polyketides, and nucleotide sequences encoding such enzymes, have now been identified and characterized. As well, synthetic versions of these nucleic acids have been designed and synthesized. The nucleotide sequences may be used to create, through breeding, selection or genetic engineering, *Cannabis* plants that overproduce or under-produce cannabinoid compounds, analogs of cannabinoid compounds or mixtures thereof. These nucleotide sequences may also be used, alone or in combination with genes encoding other steps in cannabinoid synthesis pathways, to engineer cannabinoid biosynthesis in other plants or in microorganisms (e.g. yeast, bacteria, fungi) or other prokaryotic or eukaryotic organisms or in cell-free systems. In addition, knocking out this gene in *Cannabis* could be used to block cannabinoid biosynthesis and thereby reduce production of cannabinoids.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which:

FIG. 2A depicts an assay of CsPKS/olivetol synthase with hexanoyl CoA and malonyl CoA in which HTAL (5.2 min) and an unknown compound at 5.9 min were detected. FIG. 2B depicts an assay of recombinant CsOAS with hexanoyl CoA and malonyl CoA in which no products were detected. FIG. 2C depicts an assay of CsPKS/olivetol synthase and CsOAS with hexanoyl CoA and malonyl CoA in which, in addition to HTAL (5.2 min) and an unknown compound (5.9 min), a peak corresponding to olivetolic acid was observed at 9.0 minutes.

FIG. 3A depicts an assay of CsPKS/olivetol synthase with hexanoyl CoA in which no olivetolic acid was detected but HTAL, PDAL and olivetol were present. FIG. 3B depicts an assay of CsPKS/olivetol synthase and CsOAS with hexanoyl CoA in which olivetolic acid was observed at 9 minutes in addition to HTAL, PDAL and olivetol.

FIG. 4A depicts an assay of CsOAS with butyryl CoA in which no resorcinolic acid analogs of olivetolic acid were detected. FIG. 4B depicts an assay of CsPKS/olivetol synthase and CsOAS with butyryl CoA in which the olivetolic acid analog 2,4-dihydroxy-6-propylbenzoic acid was observed at 18 minutes.

FIG. 5A depicts an assay of CsOAS with octanoyl CoA in which no resorcinolic acid analogs of olivetolic acid were detected. FIG. 5B depicts an assay of CsPKS/olivetol synthase and CsOAS with octanoyl CoA in which the olivetolic acid analog 2,4-dihydroxy-6-heptylbenzoic acid was observed at 9 minutes.

DESCRIPTION OF PREFERRED EMBODIMENTS

Figure 1:
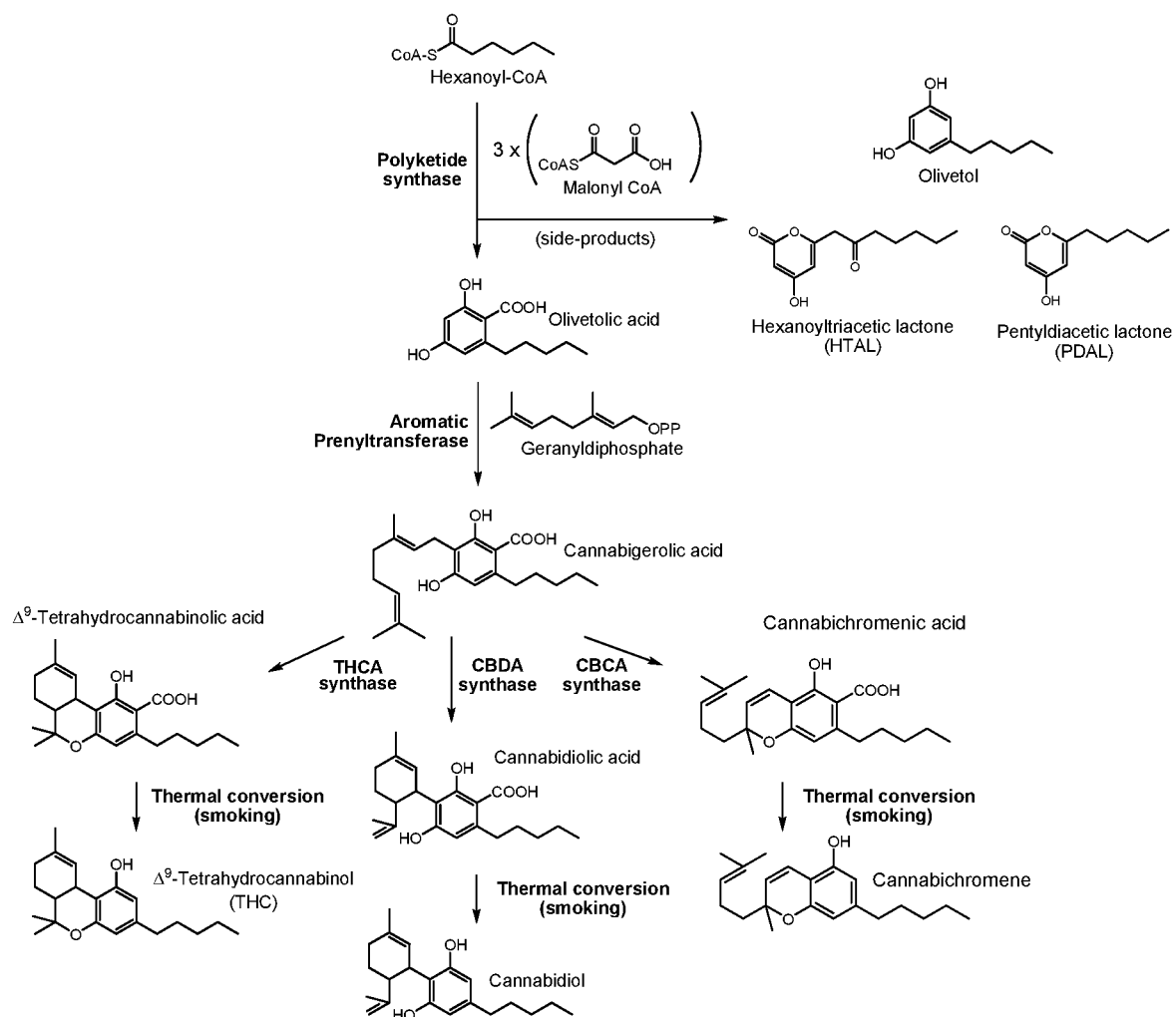
FIG. 1 depicts a proposed pathway leading to the main cannabinoid types in *Cannabis sativa*. The production of side-products by the polyketide synthase is shown. Abbreviations: THCA synthase is $\Delta^9$-tetrahydrocannabinolic acid synthase; CBDA synthase is cannabidiolic acid synthase; CBCA synthase is cannabichromenic acid synthase.

Some embodiments of the present invention relate to an isolated or purified nucleic acid molecule having SEQ ID No. 1 or having at least 75%, at least 76%, least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to SEQ ID NO: 1.

As is well known to those of skill in the art, it is possible to improve the expression of a nucleic acid sequence in a host organism by replacing the nucleic acids coding for a particular amino acid (i.e. a codon) with another codon which is better expressed in the host organism. One reason that this effect arises due to the fact that different organisms show preferences for different codons. In particular, bacterial organisms and yeast organisms prefer different codons from plants and animals. The process of altering the sequence of a nucleic acid to achieve better expression based on codon preference is called codon optimization. Statistical methods have been generated to analyze codon usage bias in various organisms and many computer algorithms have been developed to implement these statistical analyses in the design of codon optimized gene sequences (Lithwick G, Margalit H (2003) Hierarchy of sequence-dependent features associated with prokaryotic translation. *Genome Research* 13: 2665-73). Other modifications in codon usage to increase protein expression that are not dependent on codon bias have also been described (Welch et al. (2009) Design parameters to control synthetic gene expression in *Escherichia coli. PLoS ONE* 4: e7002).

Some embodiments of the invention relate to codon optimized nucleic acid molecules based on the sequence of SEQ ID No. 1. In particular, the present invention includes an isolated or purified nucleic acid molecule having SEQ ID No. 3 or having at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to SEQ ID NO: 3.

Further included are nucleic acid molecules that hybridize to the above disclosed sequences. Hybridization conditions may be stringent in that hybridization will occur if there is at least a 90%, 95% or 97% sequence identity with the nucleic acid molecule that encodes the enzyme of the present invention. The stringent conditions may include those used for known Southern hybridizations such as, for example, incubation overnight at 42° C. in a solution having 50% formamide, 5× SSC (150 mM NaCl, 15 mM trisodium citrate), 50 mM sodium phosphate (pH 7.6), 5× Denhardt's solution, 10% dextran sulfate, and 20 micrograms/milliliter denatured, sheared salmon sperm DNA, following by washing the hybridization support in 0.1×SSC at about 65° C. Other known hybridization conditions are well known and are described in Sambrook et al., Molecular Cloning: A Laboratory Manual, Third Edition, Cold Spring Harbor, N.Y. (2001).

As will be appreciated by the skilled practitioner, slight changes in nucleic acid sequence do not necessarily alter the amino acid sequence of the encoded polypeptide. It will be appreciated by persons skilled in the art that changes in the identities of nucleotides in a specific gene sequence that change the amino acid sequence of the encoded polypeptide may result in reduced or enhanced effectiveness of the genes and that, in some applications (e.g. anti-sense, co suppression, or RNAi), partial sequences often work as effectively as full length versions. The ways in which the nucleotide sequence can be varied or shortened are well known to persons skilled in the art, as are ways of testing the effectiveness of the altered genes. In certain embodiments, effectiveness may easily be tested by, for example, conventional gas chromatography. All such variations of the genes are therefore included as part of the present disclosure.

As will be appreciated by one of skill in the art, the length of the nucleic acid molecule described above will depend on the intended use. For example, if the intended use is as a primer or probe, for example for PCR amplification or for screening a library, the length of the nucleic acid molecule will be less than the full length sequence, for example, 15-50 nucleotides. In these embodiments, the primers or probes may be substantially identical to a highly conserved region of the nucleic acid sequence or may be substantially identical to either the 5' or 3' end of the DNA sequence. In some cases, these primers or probes may use universal bases in some positions so as to be 'substantially identical' but still provide flexibility in sequence recognition. It is of note that suitable primer and probe hybridization conditions are well known in the art.

Some embodiments relate to an isolated or purified polypeptide having SEQ ID NO. 2 or having at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence as set forth in SEQ ID NO: 2.

Some embodiments relate to a vector, construct or expression system containing an isolated or purified polynucleotide having at least 75% sequence identity to SEQ ID NO: 1 or SEQ ID NO: 3. As well, there is provided a method for preparing a vector, construct or expression system including such a sequence, or a part thereof, for introduction of the sequence or partial sequence in a sense or anti-sense orientation, or a complement thereof, into a cell.

In some embodiments, the isolated and/or purified nucleic acid molecules, or vectors, constructs or expression systems comprising these isolated and/or purified nucleic acid molecules, may be used to create transgenic organisms or cells of organisms that produce polypeptides which catalyze the synthesis of aromatic polyketides. Therefore, one embodiment relates to transgenic organisms, cells or germ tissues of the organism comprising an isolated and/or purified nucleic acid molecule having at least 75% sequence identity to SEQ ID NO: 1 or SEQ ID NO: 3.

Preferably, the organism is a plant, microorganism or insect. Plants are preferably of the genus *Cannabis*, for example *Cannabis sativa* L., *Cannabis indica* Lam. and *Cannabis ruderalis* Janisch. Especially preferred is *Cannabis sativa*. Microorganisms are preferably bacteria (e.g. *Escherichia coli*) or yeast (e.g. *Saccharomyces cerevisiae*). Insect is preferably *Spodoptera frugiperda*.

Organisms, cells and germ tissues of this embodiment may have altered levels of cannabinoid compounds. With reference to FIG. 1, it will be appreciated by one skilled in the art that expression or over-expression of the nucleic acid molecules of the invention will result in expression or over-expression of the enzyme that catalyzes the synthesis of aromatic polyketides (e.g. olivetolic acid) which may result in increased production of cannabinoid compounds such as cannabigerolic acid (CBGA), $\Delta^9$-tetrahydrocannabinolic acid (THCA), cannabidiolic acid (CBDA), cannabichromenic acid (CBCA), $\Delta^9$-tetrahydrocannabinol, cannabidiol, cannabichromene, etc. Similarly, depending on the substrate used, expression or over-expression of the nucleic acid molecules of the invention resulting in expression or over-expression of the enzyme that catalyzes the synthesis of aromatic polyketides may result in increased production of analogs of cannabinoid compounds, or analogs of precursors of such compounds.

Silencing of the gene in the organism, cell or tissue will result in under-expression of the enzyme which may result in accumulation of precursors such as malonyl CoA and hexanoyl CoA, and/or reduction of cannabinoids such as THCA (the precursor of THC) or CBDA (the precursor of cannabidiol (CBD)).

Expression or over-expression of the nucleic acid molecules of the invention may be done in combination with expression or over-expression of one or more other nucleic acids that encode one or more enzymes in a cannabinoid biosynthetic pathway. Some examples of other nucleic acids include: acyl CoA synthetase synthetase, a type III polyketide synthase, a polyketide cyclase, an aromatic prenyltransferase and a cannabinoid-forming oxidocyclase. Specific examples of these enzymes include hexanoyl CoA synthetase, a type III polyketide synthase/olivetol synthase, a geranylpyrophosphate:olivetolate geranyltransferase, a $\Delta^9$-tetrahydrocannabinolic acid synthase, a cannabidiolic acid synthase or a cannabichromenic acid synthase.

Expression or over-expression of the enzyme of the present invention compared to a control which has normal levels of the enzyme for the same variety grown under similar or identical conditions will result in increased levels of cannabinoid compounds, for example, 1-20%, 2-20%, 5-20%, 10-20%, 15-20%, 1-15%, 1-10%, 2-15%, 2-10%, 5-15%, or 10-15% (w/w). Cannabinoids already exceed 25% by dry weight in some *Cannabis* varieties.

Synthesis of aromatic polyketides in the presence of an enzyme polypeptide of the present invention may be accomplished in vivo or in vitro. As previously mentioned, such syntheses in vivo may be accomplished by expressing or over-expressing the nucleic acid molecule of the invention in an organism, cell or tissue. The organism, cell or tissue may naturally contain alkanoyl CoA and malonyl CoA, or the alkanoyl CoA and malonyl CoA may be provided to the organism, cell or tissue for uptake and subsequent reaction.

Synthesis in vitro can take place in a cell-free system. As part of an in vitro cell-free system, the alkanoyl CoA and malonyl CoA, the polyketide synthase/olivetolic acid synthase (CsPKS/olivetol synthase) and the polypeptide of the present invention may be mixed together in a suitable reaction vessel to effect the reaction. In vitro, the polypeptide of the present invention may be used in combination with other enzymes to effect a complete synthesis of a target compound from a precursor. For example, such other enzymes may be implicated in a cannabinoid biosynthetic pathway as described in FIG. 1.

The polypeptides of the present invention may be used, in vivo or in vitro, to synthesize analogs of cannabinoid compounds which are not naturally occurring in the host species. Such analogs can be produced using alkanoyl CoA compounds other than those used to produce natural cannabinoid compounds in plants. For example, when the short-chain acyl CoA thioesters butyryl CoA (also called n-butyryl CoA to indicate that it has a straight chain) and octanoyl CoA (also called n-octanoyl CoA to indicate that it has a straight chain) were used as substrates for the polypeptides of the present invention, resorcinolic acid analogs of cannabinoid precursors were synthesized. Use of butyryl CoA as substrates with CsOAS and CsPKS/olivetol synthase polypeptides produced the resorcinolic acid 2,4-dihydroxy-6-propylbenzoic acid and use of octanoyl CoA produced the resorcinolic acid 2,4-dihydroxy-6-heptylbenzoic acid.

Terms

In order to facilitate review of the various embodiments of the disclosure, the following explanations of specific terms are provided:

Alkanoyl CoA: An alkanoyl CoA is an aliphatic carbonyl compound having a coenzyme A moiety bonded to the carbon atom of the carbonyl group through a sulfide bridge. Preferred alkanoyl CoA compounds comprise from 2 to 6 carbon atoms in the aliphatic carbonyl part of the compound. More preferably, the alkanoyl CoA is CoA-S—C(O)—$(CH_2)_n$—$CH_3$, where n is an integer from 0 to 4. Some examples of alkanoyl CoA compounds are acetyl CoA, butyryl CoA, hexanoyl CoA and octanoyl CoA. Use of acetyl CoA provides a methyl side chain to the resulting aromatic polyketide; use of butyryl CoA provides a propyl side chain; and use of hexanoyl CoA provides a pentyl side chain. Hexanoyl CoA is especially preferred. It has been shown that cannabinoids with short side-chains exist in *Cannabis* (e.g. tetrahydrocannabivarinic acid having a propyl side-chain instead of the pentyl side-chain of THC acid (Shoyama Y, Hirano H, Nishioka I. (1984) Biosynthesis of propyl cannabinoid acid and its biosynthetic relationship with pentyl and methyl cannabinoid acids. *Phytochemistry.* 23(9): 1909-1912)).

Codon degeneracy: It will be appreciated that this disclosure embraces the degeneracy of codon usage as would be understood by one of ordinary skill in the art and as illustrated in Table 1.

TABLE 1

Codon Degeneracies

| Amino Acid | Codons |
|---|---|
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, UGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |
| START | ATG |
| STOP | TAG, TGA, TAA |

Complementary nucleotide sequence: "Complementary nucleotide sequence" of a sequence is understood as meaning any nucleic acid molecule whose nucleotides are complementary to those of a sequence disclosed herein, and whose orientation is reversed (anti-parallel sequence).

Conservative substitutions: It will be understood by one skilled in the art that conservative substitutions may be made in the amino acid sequence of a polypeptide without disrupting the three-dimensional structure or function of the polypeptide. Conservative substitutions are accomplished by the skilled artisan by substituting amino acids with similar hydrophobicity, polarity, and R-chain length for one another. Additionally, by comparing aligned sequences of homologous proteins from different species, conservative substitutions may be identified by locating amino acid residues that have been mutated between species without altering the basic functions of the encoded proteins. Table 2 provides an exemplary list of conservative substitutions.

TABLE 2

Conservative Substitutions

| Type of Amino Acid | Substitutable Amino Acids |
|---|---|
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

Degree or percentage of sequence homology: The term "degree or percentage of sequence homology" refers to degree or percentage of sequence identity between two sequences after optimal alignment. Percentage of sequence identity (or degree of identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue or nucleic acid base occurs in both sequences to yield the number of matched positions, dividing the number of matched positions by the total number of positions in the window of comparison and multiplying the result by 100 to yield the percentage of sequence identity.

Homologous isolated and/or purified sequence: "Homologous isolated and/or purified sequence" is understood to mean an isolated and/or purified sequence having a percentage identity with the bases of a nucleotide sequence, or the amino acids of a polypeptide sequence, of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7%. This percentage is purely statistical, and it is possible to distribute the differences between the two nucleotide or amino acid sequences at random and over the whole of their length. Sequence identity can be determined, for example, by computer programs designed to perform single and multiple sequence alignments.

Increasing, decreasing, modulating, altering or the like: As will be appreciated by one of skill in the art, such terms refer to comparison to a similar variety or strain grown under similar conditions but without the modification resulting in the increase, decrease, modulation or alteration. In some cases, this may be an untransformed control, a mock transformed control, or a vector-transformed control.

Isolated: As will be appreciated by one of skill in the art, "isolated" refers to polypeptides or nucleic acids that have been "isolated" from their native environment.

Nucleotide, polynucleotide, or nucleic acid sequence: "Nucleotide, polynucleotide, or nucleic acid sequence" will be understood as meaning both double-stranded or single-stranded in the monomeric and dimeric (so-called in tandem) forms and the transcription products thereof.

Sequence identity: Two amino acid or nucleotide sequences are said to be "identical" if the sequence of amino acids or nucleotides in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, Ad. App. Math 2:482 (1981), by the homology alignment algorithm of Needleman and Wunsch, J. Mol. Biol. 48:443 (1970), by the search for similarity method of Pearson and Lipman, Proc. Natl. Acad. Sci. (U.S.A.) 85:2444 (1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection.

The definition of sequence identity given above is the definition that would be used by one of skill in the art. The definition by itself does not need the help of any algorithm, said algorithms being helpful only to achieve the optimal alignments of sequences, rather than the calculation of sequence identity.

From the definition given above, it follows that there is a well defined and only one value for the sequence identity between two compared sequences which value corresponds to the value obtained for the best or optimal alignment.

Stringent hybridization: Hybridization under conditions of stringency with a nucleotide sequence is understood as meaning a hybridization under conditions of temperature and ionic strength chosen in such a way that they allow the maintenance of the hybridization between two fragments of complementary nucleic acid molecules.

Methods

Homologs of the CsOAS genes described herein obtained from other organisms, for example plants, may be obtained by screening appropriate libraries that include the homologs, wherein the screening is performed with the nucleotide sequence of the specific CsOAS genes of the invention, or portions or probes thereof, or identified by sequence homology search using sequence alignment search programs such as BLAST or FASTA.

Nucleic acid isolation and cloning is well established. Similarly, an isolated gene may be inserted into a vector and transformed into a cell by conventional techniques which are known to those of skill in the art. Nucleic acid molecules may be transformed into an organism. As known in the art, there are a number of ways by which genes, vectors, constructs and expression systems can be introduced into organisms, and a combination of transformation and tissue culture techniques have been successfully integrated into effective strategies for creating transgenic organisms. These methods, which can be used in the invention, have been described elsewhere (Potrykus I (1991) Gene transfer to plants: Assessment of published approaches and results. Annu. Rev. Plant Physiol. *Plant Mol. Biol.* 42:205-225; Vasil I K (1994) Molecular improvement of cereals. *Plant Mol. Biol.* 25: 925-937. Walden R, Wingender R (1995) Gene-transfer and plant regeneration techniques. *Trends in Biotechnology* 13:324-331; Songstad D D, Somers D A, Griesbach R J (1995) Advances in alternative DNA delivery techniques. *Plant Cell Tissue Organ Cult.* 40:1-15), and are well known to persons skilled in the art.

Suitable vectors are well known to those skilled in the art and are described in general technical references such as Pouwels et al., *Cloning Vectors. A Laboratory Manual*, Elsevier, Amsterdam (1986). Particularly suitable vectors include the Ti plasmid vectors. For example, one skilled in the art will certainly be aware that, in addition to *Agrobacterium* mediated transformation of *Arabidopsis* by vacuum infiltration (Bechtold N, Ellis J, Pelletier G (1993) In planta *Agrobacterium*-mediated gene transfer by infiltration of adult *Arabidopsis thaliana* plants. *C R Acad Sci Paris, Sciences de la vie/Life sciences* 316: 1194-1199.) or wound inoculation (Katavic V, Haughn G W, Reed D, Martin M, Kunst L (1994) In planta transformation of *Arabidopsis thaliana. Mol. Gen. Genet.* 245:363-370.), it is equally possible to transform other plant species, using *Agrobacterium* Ti-plasmid mediated transformation (e.g., hypocotyl (DeBlock M, DeBrouwer D, Tenning P (1989) Transformation of *Brassica napus* and *Brassica oleracea* using *Agrobacterium tumefaciens* and the expression of the bar and neo genes in the transgenic plants. *Plant Physiol.* 91:694-701.) or cotyledonary petiole (Moloney M M, Walker J M, Sharma K K (1989) High efficiency transformation of *Brassica napus* using *Agrobacterium* vectors. *Plant Cell Rep.* 8:238-242.) wound infection, particle bombardment/biolistic methods (Sanford J C, Klein T M, Wolf E D, Allen N (1987) Delivery of substances into cells and tissues using a particle bombardment process. *J. Part. Sci. Technol.* 5:27-37.) or polyethylene glycol-assisted, protoplast transformation methods (Rhodes C A, Pierce D A, Mettler I J, Mascarenhas D, Detmer J J (1988) Genetically transformed maize plants from protoplasts. Science 240: 204-207).

As will also be apparent to persons skilled in the art, and as described elsewhere (Meyer P (1995) Understanding and controlling transgene expression. *Trends in Biotechnology.* 13:332-337; Datla R, Anderson J W, Selvaraj G (1997) Plant promoters for transgene expression. *Biotechnology Annual Review* 3:269-296.), it is possible to utilize promoters operatively linked to the nucleic acid molecule to direct any intended up- or down-regulation of transgene expression using unregulated (i.e. constitutive) promoters (e.g., those based on CaMV35S), or by using promoters which can target gene expression to particular cells, tissues (e.g., napin promoter for expression of transgenes in developing seed cotyledons), organs (e.g., roots), to a particular developmental stage, or in response to a particular external stimulus (e.g., heat shock).

Promoters for use in the invention may be inducible, constitutive, or tissue-specific or have various combinations of such characteristics. Useful promoters include, but are not limited to constitutive promoters such as carnation etched ring virus promoter (CERV), cauliflower mosaic virus (CaMV) 35S promoter, or more particularly the double enhanced cauliflower mosaic virus promoter, comprising two CaMV 35S promoters in tandem (referred to as a "Double 35S" promoter). It may be desirable to use a tissue-specific or developmentally regulated promoter instead of a constitutive promoter in certain circumstances. A tissue-specific promoter allows for over-expression in certain tissues without affecting expression in other tissues.

The promoter and termination regulatory regions will be functional in the host cell and may be heterologous (that is, not naturally occurring) or homologous (derived from the host species) to the cell and the gene.

The termination regulatory region may be derived from the 3' region of the gene from which the promoter was obtained or from another gene. Suitable termination regions which may be used are well known in the art and include *Agrobacterium tumefaciens* nopaline synthase terminator (Tnos), *A. tumefaciens* mannopine synthase terminator (Tmas) and the CaMV 35S terminator (T35S). Particularly preferred termination regions for use in the present invention include the pea ribulose bisphosphate carboxylase small subunit termination region (TrbcS) or the Tnos termination region. Gene constructs for use in the invention may suitably be screened for activity by, for example, transformation into a host plant via *Agrobacterium* and screening for altered cannabinoid levels.

The nucleic acid molecules of the invention, or fragments thereof, may be used to block cannabinoid biosynthesis in organisms that naturally produce cannabinoid compounds. Silencing using a nucleic acid molecule of the invention may be accomplished in a number of ways generally known in the art, for example, RNA interference (RNAi) techniques, artificial microRNA techniques, virus-induced gene silencing (VIGS) techniques, antisense techniques, sense co-suppression techniques and targeted mutagenesis techniques.

RNAi techniques involve stable transformation using RNA interference (RNAi) plasmid constructs (Helliwell C A, Waterhouse P M (2005) Constructs and methods for hairpin RNA-mediated gene silencing in plants. *Methods Enzymology* 392:24-35). Such plasmids are composed of a fragment of the target gene to be silenced in an inverted repeat structure. The inverted repeats are separated by a spacer, often an intron. The RNAi construct driven by a suitable promoter, for example, the Cauliflower mosaic virus (CaMV) 35S promoter, is integrated into the plant genome and subsequent transcription of the transgene leads to an RNA molecule that folds back on itself to form a double-stranded hairpin RNA. This double-stranded RNA structure is recognized by the plant and cut into small RNAs (about 21 nucleotides long) called small interfering RNAs (siRNAs). The siRNAs associate with a protein complex (RISC) which goes on to direct degradation of the mRNA for the target gene.

Artificial microRNA (amiRNA) techniques exploit the microRNA (miRNA) pathway that functions to silence endogenous genes in plants and other eukaryotes (Schwab R, Ossowski S, Riester M, Warthmann N, Weigel D (2006) Highly specific gene silencing by artificial microRNAs in *Arabidopsis. Plant Cell* 18:1121-33; Alvarez J P, Pekker I, Goldshmidt A, Blum E, Amsellem Z, Eshed Y (2006) Endogenous and synthetic microRNAs stimulate simultaneous, efficient, and localized regulation of multiple targets in diverse species. *Plant Cell* 18:1134-51). In this method, 21 nucleotide long fragments of the gene to be silenced are introduced into a pre-miRNA gene to form a pre-amiRNA construct. The pre-amiRNA construct is transferred into the organism genome using transformation methods which would be apparent to one skilled in the art. After transcription of the pre-amiRNA, processing yields amiRNAs that target genes which share nucleotide identity with the 21 nucleotide amiRNA sequence.

In RNAi silencing techniques, two factors can influence the choice of length of the fragment. The shorter the fragment the less frequently effective silencing will be achieved, but very long hairpins increase the chance of recombination in bacterial host strains. The effectiveness of silencing also appears to be gene dependent and could reflect accessibility of target mRNA or the relative abundances of the target mRNA and the hairpin RNA in cells in which the gene is active. A fragment length of between 100 and 800 bp, preferably between 300 and 600 bp, is generally suitable to maximize the efficiency of silencing obtained. The other consideration is the part of the gene to be targeted. 5' UTR, coding region, and 3' UTR fragments can be used with equally good results. As the mechanism of silencing depends on sequence homology, there is potential for cross-silencing of related mRNA sequences. Where this is not desirable, a region with low sequence similarity to other sequences, such as a 5' or 3' UTR, should be chosen. The rule for avoiding cross-homology silencing appears to be to use sequences that do not have blocks of sequence identity of over 20 bases between the construct and the non-target gene sequences. Many of these same principles apply to selection of target regions for designing amiRNAs.

Virus-induced gene silencing (VIGS) techniques are a variation of RNAi techniques that exploits the endogenous antiviral defenses of plants. Infection of plants with recombinant VIGS viruses containing fragments of host DNA leads to post-transcriptional gene silencing for the target gene. In one embodiment, a tobacco rattle virus (TRV) based VIGS system can be used with the nucleotide sequences of the present invention.

Antisense techniques involve introducing into a plant an antisense oligonucleotide that will bind to the messenger RNA (mRNA) produced by the gene of interest. The "antisense" oligonucleotide has a base sequence complementary to the gene's messenger RNA (mRNA), which is called the "sense" sequence. Activity of the sense segment of the mRNA is blocked by the anti-sense mRNA segment, thereby effectively inactivating gene expression. Application of antisense to gene silencing in plants is described in more detail by Stam M, de Bruin R, van Blokland R, van der Hoorn R A, Mol J N, Kooter J M (2000) Distinct features of post-transcriptional gene silencing by antisense transgenes in single copy and inverted T-DNA repeat loci. *Plant J.* 21:27-42.

Sense co-suppression techniques involve introducing a highly expressed sense transgene into a plant resulting in reduced expression of both the transgene and the endogenous gene (Depicker A, Montagu M V (1997) Post-transcriptional gene silencing in plants. *Curr Opin Cell Biol.* 9: 373-82). The effect depends on sequence identity between transgene and endogenous gene.

Targeted mutagenesis techniques, for example TILLING (Targeting Induced Local Lesions IN Genomes) and "delete-a-gene" using fast-neutron bombardment, may be used to knockout gene function in an organism (Henikoff S, Till B J, Comai L (2004) TILLING. Traditional mutagenesis meets functional genomics. *Plant Physiol* 135:630-6; Li X, Lassner M, Zhang Y. (2002) Deleteagene: a fast neutron deletion mutagenesis-based gene knockout system for plants. Comp Funct Genomics. 3: 158-60). TILLING involves treating germplasm or individual cells with a mutagen to cause point mutations that are then discovered in genes of interest using a sensitive method for single-nucleotide mutation detection. Detection of desired mutations (e.g. mutations resulting in the inactivation of the gene product of interest) may be accomplished, for example, by PCR methods. For example, oligonucleotide primers derived from the gene of interest may be prepared and PCR may be used to amplify regions of the gene of interest from organisms in the mutagenized population. Amplified mutant genes may be annealed to wild-type genes to find mismatches between the mutant genes and wild-type genes. Detected differences may be traced back to the organism which had the mutant gene thereby revealing which mutagenized organism will have the desired expression (e.g. silencing of the gene of interest). These organisms may then be selectively bred to produce a population having the desired expression. TILLING can provide an allelic series that includes missense and knockout mutations, which exhibit reduced expression of the targeted gene. TILLING is touted as a possible approach to gene knockout that does not involve introduction of transgenes, and therefore may be more acceptable to consumers. Fast-neutron bombardment induces mutations, i.e. deletions, in organism genomes that can also be detected using PCR in a manner similar to TILLING.

It will be understood by one of skill in the art that the processes of the invention can also be carried out in a cell-free environment in the presence of one or more acyl CoA synthase enzymes that form alkanoyl CoA.

Embodiments of the invention are susceptible to various modifications and alternative forms in addition to the specific examples included herein. Thus, embodiments of the invention are not limited to the particular forms disclosed.

EXAMPLES

Example 1: Isolation and Characterization of CsOAS Gene and Enzyme

An Expressed Sequence Tag (EST) catalog from *Cannabis* glandular trichomes was analyzed for the highly-expressed proteins of unknown function. One unigene showed similarity to a "POP3-like protein" from *Arabidopsis* (GenBank protein Q9LUV2). The sequence of this protein (SEQ ID NO: 2) and the corresponding open reading frame (ORF) (SEQ ID NO: 1) of the nucleic acid molecule encoding the protein are given below.

```
Cannabis sativa CsOAS - 303 bp
                                        (SEQ ID NO: 1)
ATGGCAGTGAAGCATTTGATTGTATTGAAGTTCAAAGATGAAATCACAGA

AGCCCAAAAGGAAGAATTTTTCAAGACGTATGTGAATCTTGTGAATATCA

TCCCAGCCATGAAAGATGTATACTGGGGTAAAGATGTGACTCAAAAGAAT

AAGGAAGAAGGGTACACTCACATAGTTGAGGTAACATTTGAGAGTGTGGA

GACTATTCAGGACTACATTATTCATCCTGCCCATGTTGGATTTGGAGATG

TCTATCGTTCTTTCTGGGAAAAACTTCTCATTTTTGACTACACACCACGA

AAG

Cannabis sativa CsOAS - 101 aa
                                        (SEQ ID NO: 2)
MAVKHLIVLKFKDEITEAQKEEFFKTYVNLVNIIPAMKDVYWGKDVTQKN

KEEGYTHIVEVTFESVETIQDYIIHPAHVGFGDVYRSFWEKLLIFDYTPR

K
```

Example 2: Transformation of *E. coli* Cells with CsOAS and CsPKS/olivetol Synthase Genes For expression in *E. coli* cells, the open reading frames of CsPKS/olivetol synthase and CsOAS were amplified by PCR, cloned into pHIS8/GW for CsPKS/olivetol synthase or pET100 (Invitrogen) for CsOAS and transformed into *E. coli* BL21 (DE3) (Invitrogen). Cloning was verified by sequencing.

CsOAS was expressed in 200 mL terrific broth culture while CsPKS/olivetol synthase grown in a 1 L culture. Both cultures were incubated at 30° C./150 rpm shaking, induced with 0.5 μM IPTG and grown overnight. The cultures were centrifuged at 16,000 g for 20 min, and the pellets lysed by treatment with lysozyme and sonication. The cleared lysates were mixed with Talon resin (200 μL for CsOAS, 1 mL for CsPKS/olivetol synthase; Clontech), washed with 5 mL of His-tag Wash Buffer (50 mM Tris-HCl (pH 7), 150 mM NaCl, 20 mM imidazole, 10 mM β-mercaptoethanol) and the recombinant proteins eluted using His-tag Elution Buffer (20 mM Tris HCl (pH 7), 150 mM NaCl, 100 mM imidazole, 10 mM β-mercaptoethanol). The eluate was concentrated using a YM10 concentrator and the buffer exchanged to Storage Buffer (20 mM HEPES (pH 7.5), 25 mM NaCl, 10% glycerol, 5 mM DTT). The final protein solutions were quantified by using an RC/DC protein assay kit (Bio-Rad) which found protein concentrations of 0.5 mg/mL (CsOAS) and 5.6 mg/mL (CsPKS/olivetol synthase). SDS-PAGE gel analysis confirmed the purity of both proteins.

Example 3: Biochemical Activity of CsOAS Enzyme

Activity assays were performed in 50 mM HEPES buffer (pH 7.0) in the presence of 5 mM DTT, 0.2 mM hexanoyl CoA and 0.2 mM malonyl CoA. 25 μg CsPKS/olivetol synthase was used in assays which were conducted with CsPKS/olivetol synthase, whereas 5 μL of water was used as a substitute when CsPKS/olivetol synthase was not required. 10 μL of CsOAS was used in the following experiments, except in the case where CsPKS/olivetol synthase was assayed alone and 10 μL of water was used instead. The total volume of reactions was 100 μL. Reaction mixtures were incubated at 37° C. for 60 minutes with shaking. Products were extracted with ethyl acetate, dried by vacuum and resuspended in 30 μL methanol.

The products were analyzed by liquid chromatography-mass spectrometry (LC-MS) on a Waters Alliance system with a Waters Symmetry C18 3.5 μm column (2.1×100 mm). Elution was monitored by Waters PDA 2996 at 280 nM and Waters 3100 mass detector in SIR ES$^+$ mode for olivetol (180.91 Da), pentyldiacetic acid lactone (PDAL) (182.96 Da), hexanoyltriacetic acid lactone (HTAL) (224.95 Da) and olivetolic acid (224.95 Da). Dwell was set for 0.010 sec and cone voltages were set to 25 V for 180.91 Da and 224.95 Da, and 40 V for 182.96 Da. MS scan was conducted in ES$^+$ mode for masses between 150-650 Da, with a centroid scan of 5000 Da/sec. Solvent A consisted of 90% water, 10% acetonitrile with 0.1% formic acid. Solvent B consisted of 99.9% acetonitrile with 0.1% formic acid. 10 μL of sample was injected into the LC-MS and eluted isocratically using 70% solvent A for 5 min at 0.2 mL/min flow rate. A gradient continued towards 100% solvent B until 17 min was reached. The gradient returned to 70% solvent A over 3 min, where it was maintained until 25 min to re-equilibrate. Column temperature was 30° C.±5° C.

Figure 2A:
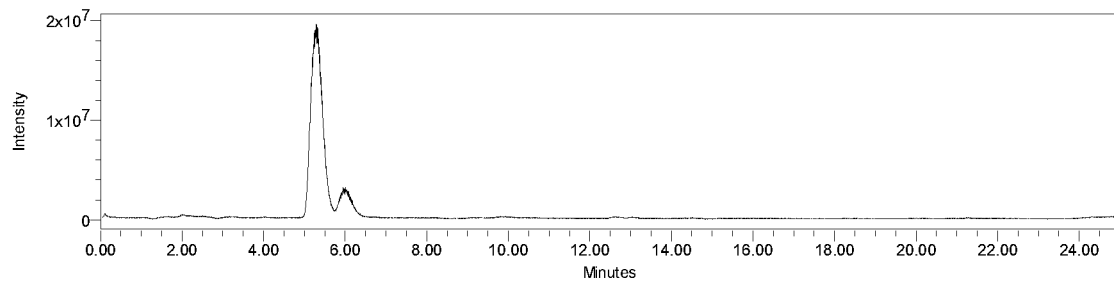
FIGS. 2A-2C depicts liquid chromatography—mass spectrometry (LC-MS) analysis of the enzymatic activity of *Cannabis sativa* polyketide synthase/olivetol synthase (CsPKS/olivetol synthase) and *Cannabis sativa* olivetolic acid synthase (CsOAS). The elution was monitored on a Waters 3100 MS in SIR ES$^+$ mode at 224.95 Da, which detects HTAL and olivetolic acid but not PDAL or olivetol.
Figure 2B:
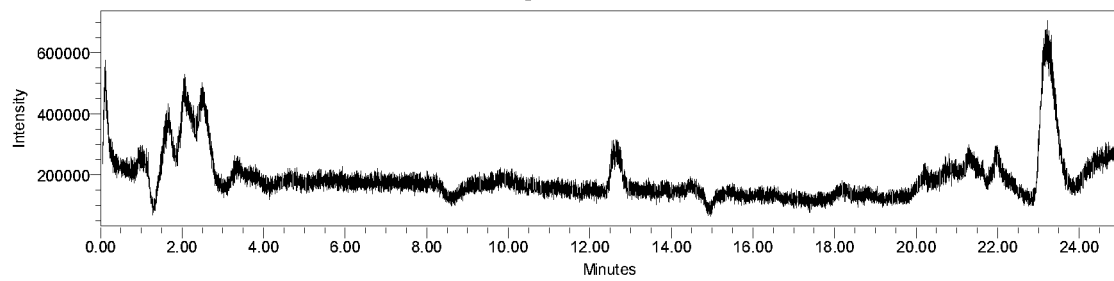
Figure 2C:
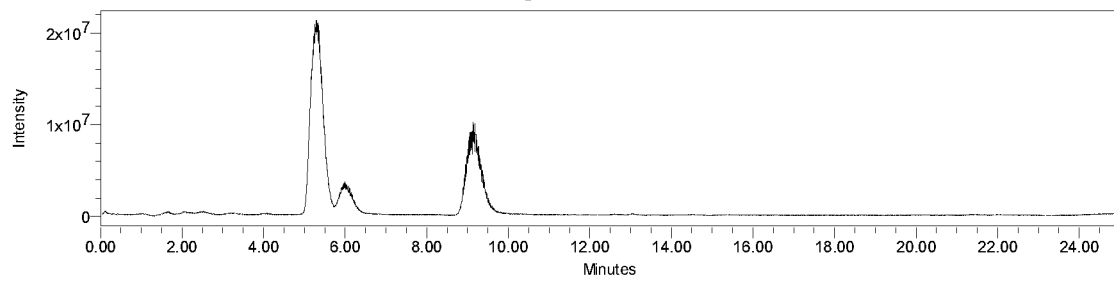

The results of the assays of recombinant proteins are shown in FIG. 2. Assayed alone, CsPKS/olivetol synthase catalyzed the formation of two pyrones (pentyldiacetic acid lactone (PDAL) and hexanoyltriacetic acid lactone (HTAL)) and olivetol which confirms the findings of Taura et al., 2009. CsOAS alone did not produce any products when tested with hexanoyl CoA and malonyl CoA. However, when CsPKS/olivetol synthase and CsOAS were assayed together, the reaction mixtures contained olivetolic acid (9.0 min). Therefore CsOAS is an enzyme that functions together with CsPKS/olivetol synthase to form olivetolic acid.

Example 4: Biochemical Activity of CsOAS Enzyme

Figure 3A:
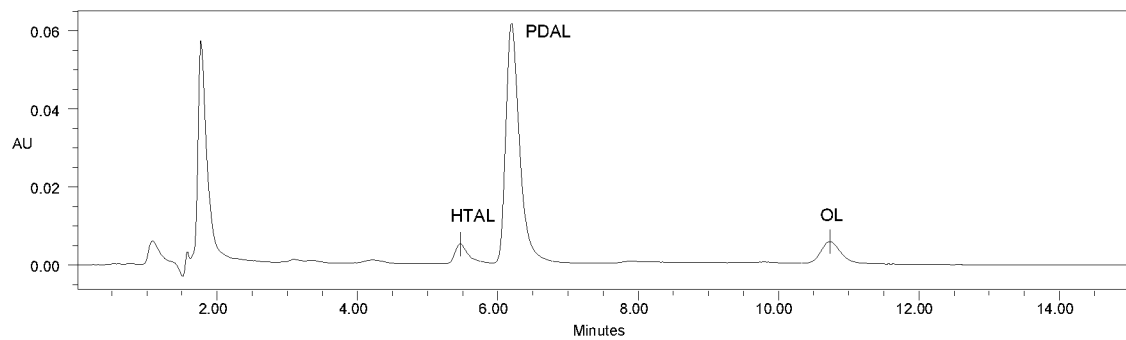
FIGS. 3A and 3B depict liquid chromatography—photo-diode array (PDA) analyses of the enzymatic activity of *Cannabis sativa* polyketide synthase/olivetol synthase (CsPKS/olivetol synthase) alone and together with *Cannabis sativa* olivetolic acid synthase (CsOAS) using hexanoyl CoA as substrate. These assays made use of the recombinant enzyme malonyl CoA synthetase (MCS) to produce malonyl CoA.
Figure 3B:
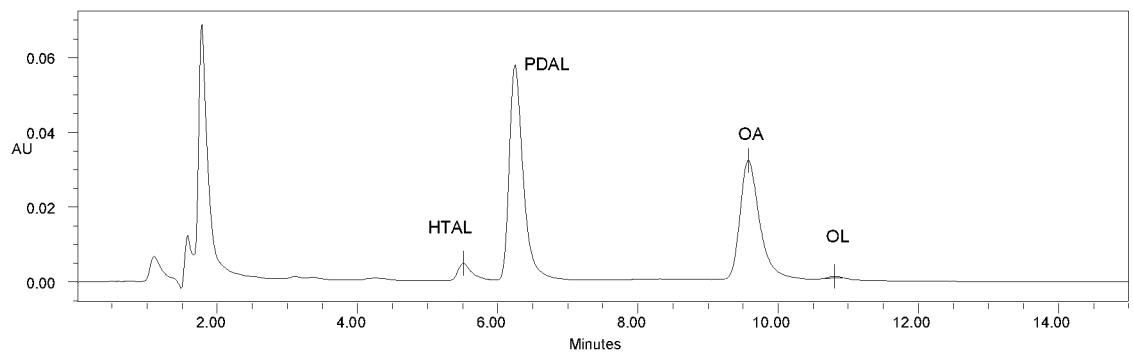

These assays made use of the recombinant enzyme malonyl CoA synthetase (MCS) to produce malonyl CoA. Activity assays were performed in 20 mM HEPES buffer (pH 7.0) in the presence of 5 mM DTT, 0.2 mM hexanoyl CoA, 2.5 mM MgCl$_2$, 0.5 mM ATP, 0.2 mM coenzyme A, 8 mM sodium malonate, 9 μg CsPKS and 11 μg malonyl CoA synthetase (MCS) with and without 16 μg of CsOAS. The total volume of the reactions was 100 μL. Reaction mixtures were incubated at 20° C. for 90 minutes with shaking. Products were extracted with ethyl acetate, dried by vacuum and resuspended in 60 μL of 70% water/30% acetonitrile. The products were analyzed by liquid chromatography-mass spectrometry (LC-MS) on a Waters Alliance system with a Waters Symmetry C18 3.5 μm column (2.1×100 mm) using 70% solvent A (90% water, 10% acetonitrile, 0.05% formic acid) and 30% solvent B (acetonitrile+0.05% formic acid) as the elution solvent. The results of the assays of recombinant proteins are shown in FIG. 3. These results shown in FIG. 3A show that CsPKS forms the two pyrones pentyldiacetic lactone (PDAL) and hexanoyltriacetic lactone (HTAL), and olivetol (OL) but not olivetolic acid. Reactions containing both CsPKS and CsOAS, shown in FIG. 3B, yield olivetolic acid (OA) in addition to the other products.

Example 5: Biochemical Activity of CsOAS Enzyme Using Butyryl CoA as Substrate

These assays made use of the recombinant enzyme malonyl CoA synthetase (MCS) to produce malonyl CoA. Activity assays were performed in 20 mM HEPES buffer (pH 7.0) in the presence of 5 mM DTT, 0.2 mM butyryl CoA, 2.5 mM $MgCl_2$, 0.5 mM ATP, 0.2 mM coenzyme A, 8 mM sodium malonate, 9 µg CsPKS and 11 µg malonyl CoA synthetase (MCS) with and without 16 µg of CsOAS. The total volume of the reactions was 100 µL. Reaction mixtures were incubated at 20° C. for 90 minutes with shaking. Products were extracted with ethyl acetate, dried by vacuum and resuspended in 60 µL of 70% water/30% acetonitrile. The products were analyzed by liquid chromatography-mass spectrometry (LC-MS) on a Waters Alliance system with a Waters Symmetry C18 3.5 µm column (2.1×100 mm) using 90% solvent A (90% water, 10% acetonitrile, 0.05% formic acid) and 10% solvent B (acetonitrile+0.05% formic acid) as the elution solvent. The results of the assays of recombinant proteins are shown in FIG. 4.

Figure 4A:
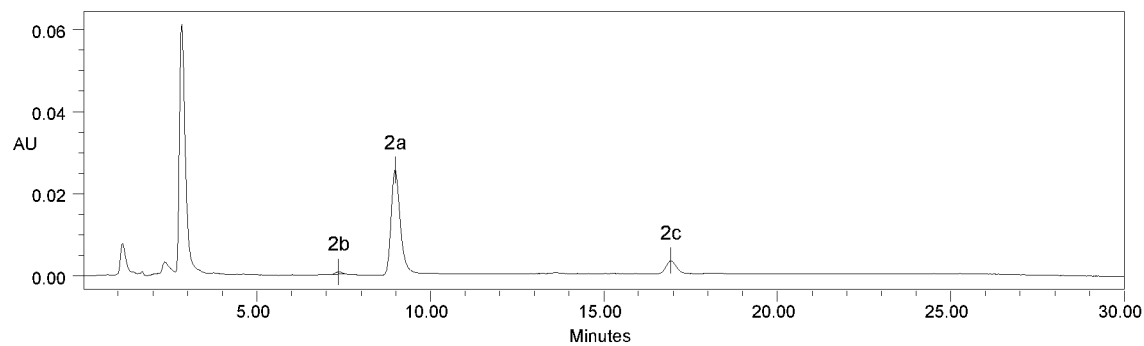
FIGS. 4A-4B depict liquid chromatography—photodiode array (PDA) analysis of the enzymatic activity of *Cannabis sativa* polyketide synthase/olivetol synthase (CsPKS/olivetol synthase) alone and together with *Cannabis sativa* olivetolic acid synthase (CsOAS) using butyryl-CoA as substrate. These assays made use of the recombinant enzyme malonyl CoA synthetase (MCS) to produce malonyl CoA.

The assays with butyryl CoA and CsPKS alone are shown in FIG. 4A, which shows that the two pyrones, 2a and 2b, and the resorcinol, 2c, are formed, but not the olivetolic acid analog, resorcinolic acid 2d. The structure of each of these compounds is shown below.

Figure 4B:
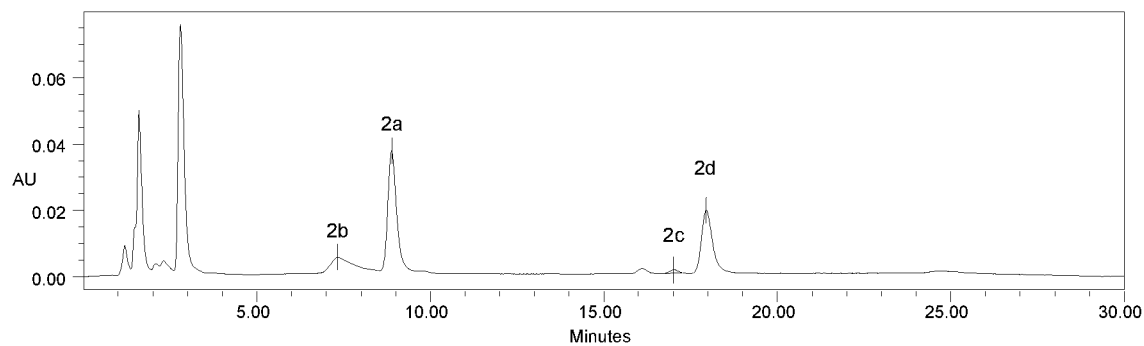

The assays with butyryl CoA containing CsPKS and CsOAS are shown in FIG. 4B, which shows that each of 2a, 2b, 2c, and the olivetolic acid analog, 2d, is formed.

Example 6: Biochemical Activity of CsOAS Enzyme Using Octanoyl CoA as Substrate

These assays made use of the recombinant enzyme malonyl CoA synthetase (MCS) to produce malonyl CoA. Activity assays were performed in 20 mM HEPES buffer (pH 7.0) in the presence of 5 mM DTT, 0.2 mM octanoyl CoA, 2.5 mM $MgCl_2$, 0.5 mM ATP, 0.2 mM coenzyme A, 8 mM sodium malonate, 9 µg CsPKS and 11 µg malonyl CoA synthetase (MCS) with and without 16 µg of CsOAS. The total volume of the reactions was 100 µL. Reaction mixtures were incubated at 20° C. for 90 minutes with shaking. Products were extracted with ethyl acetate, dried by vacuum and resuspended in 60 µL of 70% water/30% acetonitrile. The products were analyzed by liquid chromatography-mass spectrometry (LC-MS) on a Waters Alliance system with a Waters Symmetry C18 3.5 µm column (2.1×100 mm) using 60% solvent A (90% water, 10% acetonitrile, 0.05% formic acid) and 40% solvent B (acetonitrile+0.05% formic acid) as the elution solvent. The results of the assays of recombinant proteins are shown in FIG. 5.

Figure 5A:
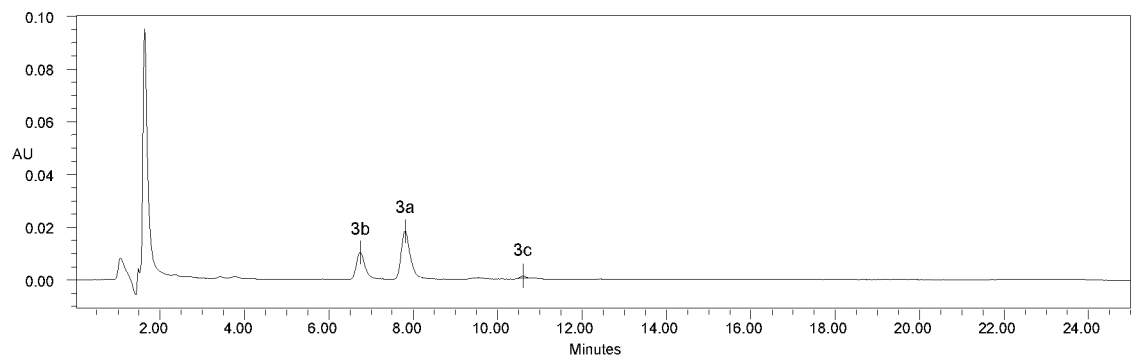
FIGS. 5A and 5B depicts a liquid chromatography—photodiode array (PDA) analysis of the enzymatic activity of *Cannabis sativa* polyketide synthase/olivetol synthase CsPKS/olivetol synthase) alone and together with *Cannabis sativa* olivetolic acid synthase (CsOAS) using octanoyl CoA as substrate. These assays made use of the recombinant enzyme malonyl CoA synthetase (MCS) to produce malonyl CoA.

The assays with octanoyl CoA and CsPKS alone are shown in FIG. 5A, which shows that two pyrones, 3a and 3b, and the resorcinol, 3c, are formed but not the olivetolic acid analog, resorcinolic acid, 3d. The structure of each of these compounds is shown below.

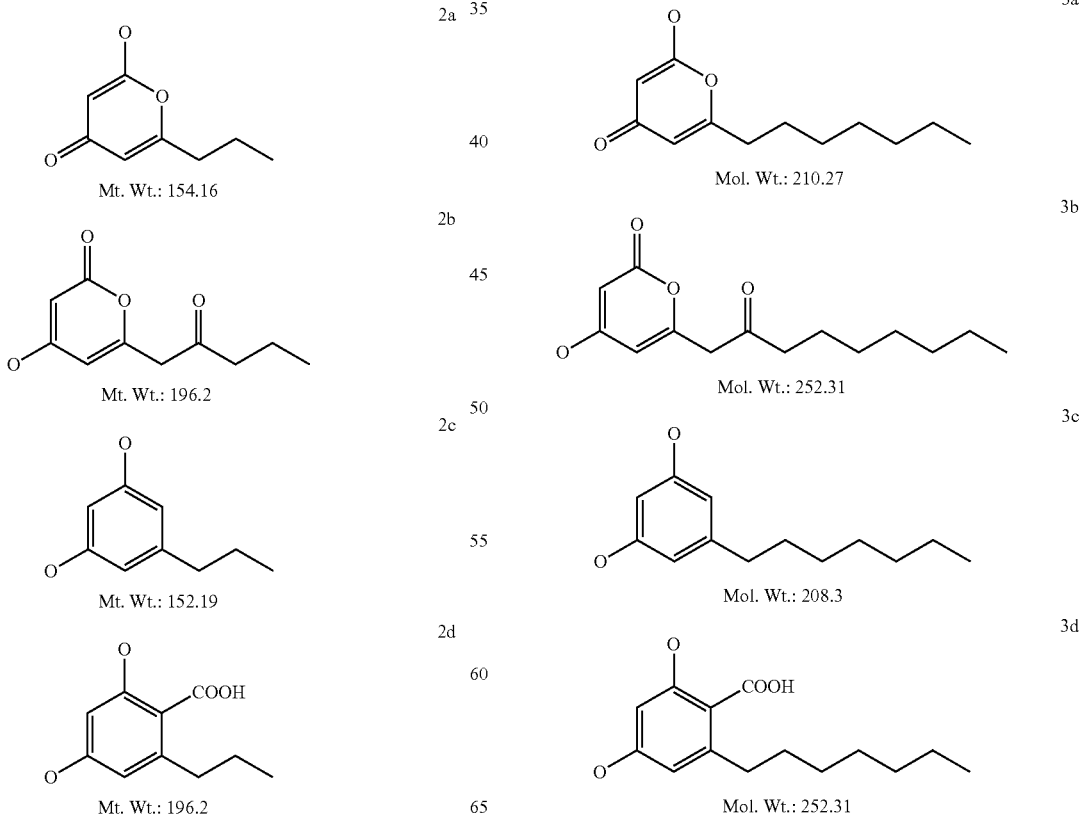

Figure 5B:
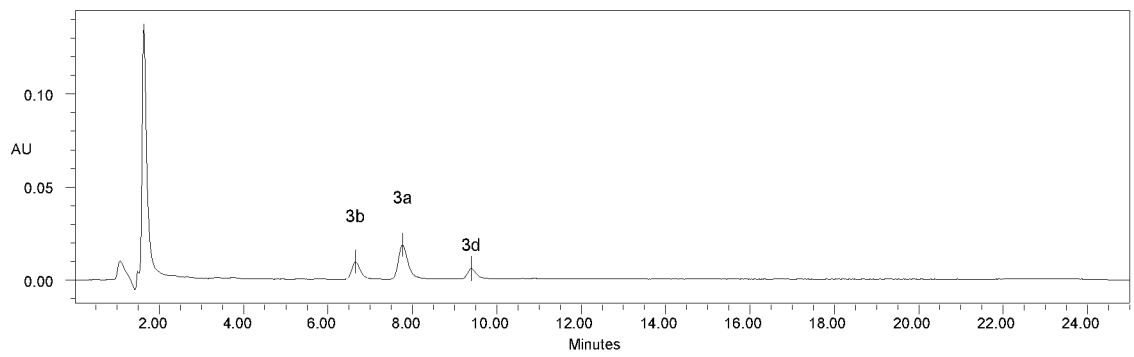

The assays with octanoyl CoA containing CsPKS and CsOAS are shown in FIG. 5B which shows that 3a, 3b and the olivetolic acid analog, 3d, is formed.

Example 7: Design and Synthesis of Codon-Optimized Nucleic Acid Encoding CsOAS Enzyme The codon-optimized sequence based on SEQ ID No. 1 (OAS opt) was synthesized using codons known to provide higher expression in *E. coli*.

The OAS_opt sequence is:

(SEQ ID NO: 3)
ATGGCGGTTAAGCACTTGATCGTCCTGAAGTTCAAAGACGAGATTACTGA

GGCCCAAAAAGAAGAGTTTTTCAAAACCTACGTGAATCTGGTGAACATCA

TTCCGGCGATGAAGGACGTTTACTGGGGTAAAGATGTGACCCAGAAGAAC

AAAGAAGAGGGCTATACCCATATTGTCGAAGTTACGTTTGAGAGCGTCGA

AACCATCCAGGACTATATCATTCATCCGGCACACGTTGGCTTCGGTGATG

TGTATCGCAGCTTCTGGGAGAAACTGCTGATCTTTGATTACACGCCGCGT

AAG.

The DNA sequence of OAS_opt is 79% identical to SEQ ID NO: 1.

Example 8: Transformation of *E. coli* Cells with Codon-Optimized CsOAS

CsOAS_opt was PCR amplified with Phusion polymerase (Finnzymes) from a plasmid clone using the primers CsOAS_opt forward (5'-ATGGCGGTTAAGCACTTGATC-3') (SEQ ID NO: 4) and CsOAS_opt reverse (5'-TTACTTACGCGGCGTGTAATC-3') (SEQ ID NO: 5). PCR products were purified and cloned into the pCR8/GW/TOPO entry vector (Invitrogen). After transformation into *E. coli* TOP10 cells (Invitrogen), individual clones were verified by sequencing. The CsOAS_opt was recombined into the pHIS8/GW destination vector using LR recombinase (Invitrogen). The LR reaction products were transformed into TOP10 cells and verified by sequencing.

pHIS8/GW-CsOAS_opt was transformed into *E. coli* Rosetta 2 cells (Merck). An individual colony was used to inoculate 5 mL liquid LB medium containing 50 μg/mL kanamycin and grown overnight at 37° C. This culture was used to inoculate 500 mL of overnight autoinduction medium (TB broth containing 0.05% glucose, 0.2% α-lactose monohydrate, 50 mM $Na_2HPO_4$, 50 mM $KH_2PO_4$, 25 mM $(NH_4)_2SO_4$, 1 mM $MgSO_4$) containing 50 μg/mL kanamycin. The culture was incubated for 16 hours at 30° C. before adding 0.5 mL 500 mM IPTG and allowing cultures to grow another 4 hours at 30° C.

Cultures were centrifuged for 10 minutes at 10 000 g at 4° C. The supernatant was discarded; the pellet was collected and frozen at −80° C. The pellet was thawed on ice in the presence of 80 mL of His-tag lysis buffer (50 mM Tris-HCl (pH 7.0), 500 mM NaCl, 2.5 mM imidazole, 750 μg/mL lysozyme, 10 mM β-mercaptoethanol) for 1 hour. The culture was sonicated on ice and the cell debris pelleted by centrifugation at 16,000 g for 20 minutes. The lysate (supernatant) was decanted and tumbled at 4° C. for 30 minutes in the presence of 0.5 mL suspension volume of Talon resin (Clontech) followed by centrifugation for 2 minutes at 1000 g. After removal of the lysate, the Talon resin was washed using 5 mL of His-tag wash buffer (50 mM Tris-HCl (pH 7.0), 150 mM NaCl, 20 mM imidazole, 10 mM β-mercaptoethanol) followed by centrifugation (1000 g for 30 seconds). This washing process was repeated four times. The Talon resin was transferred to a 5 mL gravity-flow column, rinsed with 5 mL His-tag wash buffer, and the protein was eluted using 5 mL of His-tag elution buffer (20 mM Tris-HCl (pH 7.0), 150 mM NaCl, 200 mM imidazole, 10 mM 3-mercaptoethanol). The flow-through was concentrated to 1 mL using a 15 mL 5000 MWCO Amicon Ultra concentrator (Millipore) which was centrifuged for 30 minutes at 2800 g at 4° C. Buffer transfer was accomplished by applying the sample to a 5 mL Zeba Desalt Spin Column (Thermo Scientific) equilibrated with an appropriate storage buffer (20 mM HEPES (pH 7.0), 25 mM NaCl, 10% glycerol, 5 mM DTT) and centrifuging at 1000 g for 2 minutes at 4° C. The 1.5 mL solution was further concentrated to 300 μL using a 0.5 mL 10 000 MWCO Amicon Ultra concentrator (Millipore) that was centrifuged for 10 minutes at 10 000 g. The protein sample was quantified using an RC/DC protein assay kit (Biorad). The CsOAS_opt protein was determined to be pure by SDS-PAGE electrophoresis.

Example 9: Biochemical Activity of Codon-Optimized CsOAS

Figure 6:
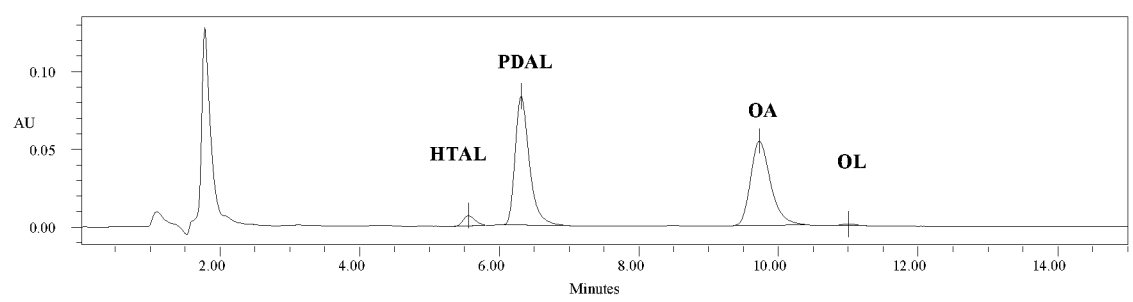
FIG. 6 depicts a liquid chromatography—photodiode array (PDA) analysis of the enzymatic activity of *Cannabis sativa* polyketide synthase/olivetol synthase together with a codon optimized *Cannabis sativa* olivetolic acid synthase (CsOAS). This assay made use of the recombinant enzyme malonyl CoA synthetase (MCS) to produce malonyl CoA. The assay used *Cannabis sativa* polyketide synthase/olivetol synthase, MCS and CsOAS with hexanoyl CoA. Olivetolic acid was observed at 9.5 minutes.

These assays made use of the recombinant enzyme malonyl CoA synthetase (MCS) to produce malonyl CoA. Activity assays were performed in 20 mM HEPES buffer (pH 7.0) in the presence of 5 mM DTT, 0.2 mM hexanoyl CoA, 2.5 mM $MgCl_2$, 0.5 mM ATP, 0.2 mM coenzyme A, 8 mM sodium malonate, 9 μg CsPKS and 11 μg malonyl CoA synthetase (MCS) with 16 μg of CsOAS_opt. The total volume of reactions was 100 μL. Reaction mixtures were incubated at 20° C. for 90 minutes with shaking. Products were extracted with ethyl acetate, dried by vacuum and resuspended in 60 μL of 70% water/30% acetonitrile. The products were analyzed by liquid chromatography-mass spectrometry (LC-MS) on a Waters Alliance system with a Waters Symmetry C18 3.5 μm column (2.1×100 mm) using 70% solvent A (90% water, 10% acetonitrile, 0.05% formic acid) and 30% solvent B (acetonitrile+0.05% formic acid) as the elution solvent. The results of the assays of recombinant proteins are shown in FIG. 6. These results show that reactions containing both CsPKS and codon-optimized CsOAS yield olivetolic acid (OA) in addition to PDAL, HTAL and olivetol (OT).

The present invention provides genes which encode a polyketide synthase enzyme from *Cannabis*. These genes could be used to create, through breeding, targeted mutagenesis or genetic engineering, *Cannabis* plants with enhanced cannabinoid production. In addition, inactivating or silencing a gene of the invention in *Cannabis* could be used to block cannabinoid biosynthesis and thereby reduce production of cannabinoids such as THCA, the precursor of THC, in *Cannabis* plants (e.g. industrial hemp). The genes of the present invention could be used, in combination with genes encoding other enzymes in the cannabinoid pathway, to engineer cannabinoid biosynthesis in other plants or in microorganisms or in cell-free systems, or to produce analogs of cannabinoid compounds or analogs of cannabinoid precursors Throughout the present disclosure, reference is made to publications, contents of the entirety of each of which are incorporated by this reference.

Other advantages that are inherent to the invention are obvious to one skilled in the art. The embodiments are described herein illustratively and are not meant to limit the scope of the invention as claimed. Variations of the foregoing embodiments will be evident to a person of ordinary skill and are intended by the inventors to be encompassed by the following claims.

The invention claimed is:

1. A process of synthesizing a naturally-occurring cannabinoid compound or a non-naturally occurring analog of a cannabinoid compound in a microorganism comprising expressing a nucleic molecule that encodes a polypeptide with at least 95% sequence identity to SEQ ID NO: 2 or that is a conservatively substituted amino acid sequence of the sequence set forth in SEQ ID NO: 2 and having polyketide cyclase activity, in the microorganism in the presence of a type III polyketide synthase enzyme, an alkanoyl CoA and malonyl CoA.

2. The process of claim 1, wherein the microorganism is a yeast or a bacteria.

3. The process of claim 1, wherein the microorganism is *Saccharomyces cerevisiae* yeast or *E. coli*.

4. The process of claim 1, wherein the nucleic acid molecule is expressed or over-expressed in combination with expression or over-expression of one or more other nucleic acids that encode one or more enzymes in a cannabinoid biosynthetic pathway.

5. The process of claim 4, wherein the one or more enzymes in a cannabinoid biosynthetic pathway is one or more of an acyl CoA synthetase, a polyketide cyclase, an aromatic prenyltransferase or a cannabinoid-forming oxidocylase.

6. The process of claim 5, wherein the one or more enzymes in a cannabinoid biosynthetic pathway is one or more of a hexanoyl CoA synthetase, a geranylpyrophosphate:olivetolate geranyltransferase, a Δ9-tetrahydrocannabinolic acid synthase, a cannabidiolic acid synthase or a cannabichromenic acid synthase.

7. The process of claim 1, wherein the cannabinoid compound is one or more of cannabigerolic acid, Δ9-tetrahydrocannabinolic acid, cannabidiolic acid, cannabichromenic acid, Δ9-tetrahydrocannabinol, cannabidiol or cannabichromene or an analog thereof comprising a side-chain of 1 to 9 carbon atoms in length.

8. The process of claim 1, wherein the alkanoyl CoA is CoA-S—C(O)—(CH2)n-CH3, where n is an integer from 0 to 4.

9. The process of claim 8, wherein the alkanoyl CoA comprises hexanoyl CoA.

10. The process of claim 1, wherein the type III polyketide synthase enzyme is polyketide synthase/olivetol synthase.

11. The process of claim 1, wherein the nucleic acid molecule has a sequence of SEQ ID NO: 1 or 3.

* * * * *